(12) United States Patent
Arcot et al.

(10) Patent No.: US 11,976,275 B2
(45) Date of Patent: May 7, 2024

(54) GENERATION OF DOUBLE-STRANDED DNA TEMPLATES FOR SINGLE MOLECULE SEQUENCING

(71) Applicants: Roche Sequencing Solutions, Inc., Pleasanton, CA (US); Kapa Biosystems, Inc., Wilmington, MA (US)

(72) Inventors: Aruna Arcot, Fremont, CA (US); Daleen Badenhorst, Wellington (CA); Jenny A. Johnson, Castro Valley, CA (US); Martin Ranik, Kenilworth (ZA); Persis Wadia, Fremont, CA (US)

(73) Assignees: KAPA BIOSYSTEMS, INC., Wilmington, MA (US); ROCHE SEQUENCING SOLUTIONS, INC., Pleasanton, CA (US)

( * ) Notice: Subject to any disclaimer, the term of this patent is extended or adjusted under 35 U.S.C. 154(b) by 822 days.

(21) Appl. No.: 17/003,747

(22) Filed: Aug. 26, 2020

(65) Prior Publication Data

US 2021/0163927 A1   Jun. 3, 2021

Related U.S. Application Data

(63) Continuation of application No. PCT/EP2019/055015, filed on Feb. 28, 2019.

(60) Provisional application No. 62/685,817, filed on Jun. 15, 2018.

(51) Int. Cl.
| | |
|---|---|
| *C12N 15/10* | (2006.01) |
| *C12Q 1/6855* | (2018.01) |
| *C12Q 1/6874* | (2018.01) |

(52) U.S. Cl.
CPC ....... *C12N 15/1068* (2013.01); *C12Q 1/6855* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 6,958,225 B2 | 10/2005 | Dong | |
| 2007/0172839 A1 | 7/2007 | Smith | |
| 2009/0005252 A1* | 1/2009 | Drmanac et al. | .... C12Q 1/6874 506/3 |

(Continued)

FOREIGN PATENT DOCUMENTS

| | | |
|---|---|---|
| JP | H08-299 | 1/1996 |
| WO | 2012/012037 A1 | 1/2012 |

(Continued)

OTHER PUBLICATIONS

Mamanova et al., "Target-enrichment strategies for next-generation sequencing," Nat. Methods 2010, 7:111-118. (Year: 2010).*

(Continued)

*Primary Examiner* — Kaijiang Zhang
(74) *Attorney, Agent, or Firm* — Eric Grant Lee; Olga Zimmerman

(57) ABSTRACT

The invention is a novel method of sequencing nucleic acids involving making and sequencing a library of double stranded target nucleic acids containing a linear partially single-stranded adaptor.

13 Claims, 4 Drawing Sheets

Specification includes a Sequence Listing.

(56) References Cited

U.S. PATENT DOCUMENTS

2015/0284712 A1* 10/2015 Kurihara et al. .... C12Q 1/6855
506/41
2016/0230222 A1 8/2016 Liu
2016/0289737 A1* 10/2016 Belyaev ............... C12Q 1/6869
2018/0208966 A1 7/2018 Ilik

FOREIGN PATENT DOCUMENTS

| WO | 2017/162754 A1 | 9/2017 | |
| WO | WO-2017168332 A1 * | 10/2017 | ........... C12Q 1/6806 |
| WO | 2018/015365 A1 | 1/2018 | |
| WO | 2019/166530 A1 | 9/2019 | |

OTHER PUBLICATIONS

Do et al., "Sequence Artifacts in DNA from Formalin-Fixed Tissues: Causes and Strategies for Minimization," Clin. Chem. 2015, 61: 64-71. (Year: 2015).*
International Searching Authority, "International Preliminary Report on Patentability" for International Patent Application No. PCT/EP2019/055015 (dated Sep. 8, 2020).
International Searching Authority, "International Search Report" for International Patent Application No. PCT/EP2019/055015 (dated Sep. 6, 2019).
International Searching Authority, "Written Opinion of the International Searching Authority" for International Patent Application No. PCT/EP2019/055015 (dated Sep. 6, 2019).
Rohland, N et al., Cost-effective, high-throughput DNA sequencing libraries for multiplexed target capture, Genome Research, (2012), pp. 939-946, vol. 22 Issue 5.

* cited by examiner

FIGURE 1

← Sequencing primer binds
TACTGACTGTCCTCCTCCTCCGTT*T*T*T
/
/5phos/ATCTCTCTC
TTAGAGAGAG

SEQUENCE LISTING

<160> NUMBER OF SEQ ID NOS: 2

<210> SEQ ID NO 1
<211> LENGTH: 36
<212> TYPE: DNA
<213> ORGANISM: Artificial Sequence

```
-continued

<220> FEATURE:
<223> OTHER INFORMATION: Description of Artificial Sequence: Synthetic
      oligonucleotide

<400> SEQUENCE: 1
atctctctct actgactgtc ctcctcctcc gttttt                                      36

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gagagagatt                                                                    10
```

GENERATION OF DOUBLE-STRANDED DNA TEMPLATES FOR SINGLE MOLECULE SEQUENCING

CROSS-REFERENCE TO RELATED APPLICATIONS

This application is a continuation of International Application Ser. No. PCT/EP2019055015 filed on Feb. 28, 2019, which claims priority to a U.S. Provisional Application Ser. No. filed on Jun. 15, 2018, both of which are incorporated herein by reference.

SEQUENCE LISTING

The instant application contains a Sequence Listing which has been submitted electronically in ASCII format and is hereby incorporated by reference in its entirety. Said ASCII copy, created on Jan. 26, 2021, is named 34426US1Seq.txt and is 888 bytes in size.

FIELD OF THE INVENTION

The invention relates to the field of nucleic acid analysis and more specifically, to preparing templates for nucleic acid sequencing.

BACKGROUND OF THE INVENTION

Single molecule nucleic acid sequencing including nanopore sequencing typically utilizes circular templates. See U.S. Pat. Nos. 7,302,116 and 8,153,375. Linear nucleic acids are converted into a circular form for amplification and subsequent detection and quantification, see U.S. Pat. No. RE44,265. The circular template configuration is not ideal for long target molecules where linear conformation is preferred. The invention is a method to produce and sequence a library of linear target sequences using a novel adaptor design. The method has multiple advantages described in detail below.

SUMMARY OF THE INVENTION

In one embodiment, the invention is a method of separately sequencing each strand of a double stranded target nucleic acid comprising the steps of: in a reaction mixture, joining a double stranded target nucleic acid to adaptors to form an adapted target nucleic acid wherein the adaptor comprises a shorter strand and a longer strand annealed together forming a double-stranded and a single-stranded region, the single-stranded region comprising only one unpaired strand, and wherein the single-stranded region comprises a primer binding site; annealing a primer to the primer binding site in each adaptor; extending the primer thereby sequencing each strand of the adapted target nucleic acid. The joining to the adaptor may be by ligation. The adaptor may comprise at least one barcode. The adaptor may comprise at least one modified nucleotide in the double-stranded region. The modified nucleotide may be a 5'-phosphorylated terminal nucleotide, a phosphorothioate group or may modify melting temperature of the double-stranded region of the adaptor. In some embodiments, the method further comprises a target enrichment step, e.g., by capture via target-specific probes bound to solid support or by amplification with target-specific primers. In some embodiments, the method further comprises a step of contacting the reaction mixture with a DNA damage-specific cleavage agent selected from glycosylase and endonuclease, thereby cleaving damaged DNA. In some embodiments, the target nucleic acid comprises a concatenate of two or more copies of the target sequence. In some embodiments, the method further comprises a step of building a consensus sequence of the target nucleic acid from the sequence of the concatenate.

In another embodiment, the invention is a method of making a library of nucleic acids from double stranded target nucleic acids in a sample, the method comprising in a reaction mixture, joining the double stranded target nucleic acids to an adaptor to form adapted target nucleic acids wherein the adaptor comprises a shorter strand and a longer strand annealed together forming a double-stranded and a single-stranded region, wherein the single stranded region comprises only one single strand and wherein the single-stranded region comprises a primer binding site.

In yet another embodiment, the invention is a method of determining the sequence of a library of target nucleic acid in a sample, the method comprising the steps of: forming a library of single stranded circular target nucleic acids as described in the preceding paragraph; annealing a primer to the primer binding site in each adapted target nucleic acid, extending the primer thereby sequencing each strand of the target nucleic acids in the library.

In yet another embodiment, the invention is a method of sequencing a double stranded target nucleic acid comprising the steps of: in a reaction mixture, amplifying a target nucleic acid with a pair of target-specific primers thereby forming an amplicon; joining the amplicon to an adaptor to form an adapted target nucleic acid, wherein the adaptor comprises a shorter strand and a longer strand annealed together forming a double-stranded and a single-stranded region, wherein the single stranded region comprises only one single strand and wherein the single-stranded region comprises a primer binding site; annealing a sequencing primer to the primer binding site; extending the primer thereby sequencing the target nucleic acid.

In yet another embodiment, the invention is a method of making a library of target nucleic acids comprising the steps of: in a reaction mixture, amplifying target nucleic acids with a pair of target-specific primers thereby forming amplicons; joining the amplicons to adaptors to form adapted target nucleic acids wherein the adaptors comprise annealed shorter strand and a longer strand wherein the wherein the single stranded region comprises only one single strand and further comprises a primer binding site.

In yet another embodiment, the invention is a method of determining the sequence of a library of target nucleic acid in a sample, the method comprising the steps of: forming a library of adapted target nucleic acids as described in the preceding paragraph; annealing a primer to the primer binding site in each adapted target nucleic acid; extending the primer thereby sequencing each target nucleic acid in the library.

BRIEF DESCRIPTION OF THE DRAWINGS

FIG. 1 illustrates the novel adaptor, also represented by Seq. Id. No: 1+2

DETAILED DESCRIPTION OF THE INVENTION

Definitions

Figure 2:
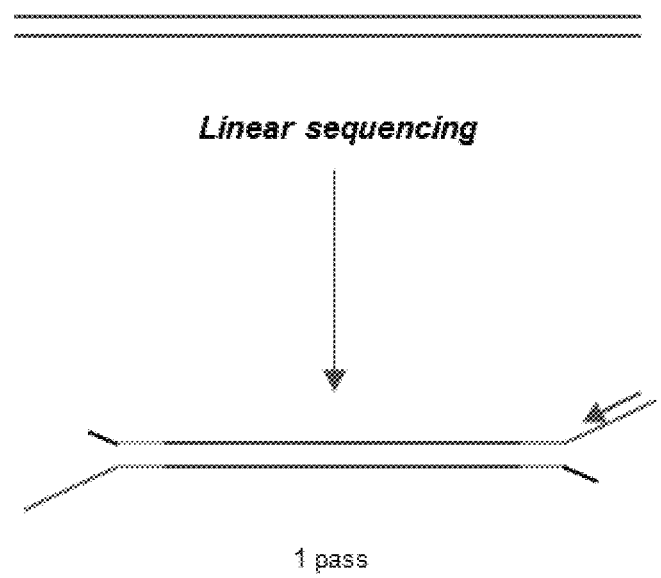
FIG. 2 illustrates sequencing a single long target sequence with the adaptor shown in FIG. 1.

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

The term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non natural bases. Some examples of non-natural bases include those described in, e.g., Seela et al., (1999) *Helv. Chim. Acta* 82:1640. The non-natural bases may have a particular function, e.g., increasing the stability of the nucleic acid duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. Oligonucleotides are prepared by any suitable method known in the art, for example, by a method involving direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859.1862; Matteucci et al. (1981) *J. Am. Chem. Soc.* 103:3185-3191.

The term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion.

The term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified. Barcodes can be incorporated into various nucleic acids. Barcodes are sufficiently long e.g., 2, 5, 20 nucleotides, so that in a sample, the nucleic acids incorporating the barcodes can be distinguished or grouped according to the barcodes.

The term "multiplex identifier" or "MID" refers to a barcode that identities a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The term "unique molecular identifier" or "UID" refers to a barcode that identifies a nucleic acid to which it is attached. All or substantially all the target nucleic acids from the same sample will have different UIDs. All or substantially all of the progeny (e.g., amplicons) derived from the same original target nucleic acid will share the same UID.

The term "universal primer" and "universal priming binding site" or "universal priming site" refer to a primer and primer binding site present in (typically, through in vitro addition to) different target nucleic acids. The universal priming site is added to the plurality of target nucleic acids using adaptors or using target-specific (non-universal) primers having the universal priming site in the 5'-portion. The universal primer can bind to and direct primer extension from the universal priming site.

More generally, the term "universal" refers to a nucleic acid molecule (e.g., primer or other oligonucleotide) that can be added to any target nucleic acid and perform its function irrespectively of the target nucleic acid sequence. The universal molecule may perform its function by hybridizing to the complement, e.g., a universal primer to a universal primer binding site or a universal circularization oligonucleotide to a universal primer sequence.

As used herein, the terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "amplification" refers to a process of making additional copies of the target nucleic acid. Amplification can have more than one cycle, e.g., multiple cycles of exponential amplification. Amplification may have only one cycle (making a single copy of the target nucleic acid). The copy may have additional sequences, e.g., those present in the primers used for amplification. Amplification may also produce copies of only one strand (linear amplification) or preferentially one strand (asymmetric PCR).

The term "sequencing" refers to any method of determining the sequence of nucleotides in the target nucleic acid.

The invention is a method of generating double stranded sequence templates suitable for single molecule long-read sequencing. As compared to existing library preparation methods, e.g., those utilizing circular templates (see U.S. Pat. Nos. 7,302,146 and 8,153,375) the method of the present invention is especially advantageous for long amplicons.

The present invention comprises detecting a target nucleic acid in a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or fecal samples). The sample may comprise whole blood or blood fractions where tumor cells may be present. In some embodiments, the sample, especially a liquid sample may comprise cell-free material such as cell-free DNA or RNA including cell-free tumor DNA or tumor RNA. The present invention is especially suitable for analyzing rare and low quantity targets. In some embodiments, the sample is a cell-free sample, e.g., cell-free blood-derived sample where cell-free tumor DNA or tumor RNA are present. In other embodiments, the sample is a cultured sample, e.g., a culture or culture supernatant containing or suspected to contain an infectious agent or nucleic acids derived from the infectious agent. In some embodiments, the infectious agent is a bacterium, a protozoan, a virus or a mycoplasma.

A target nucleic acid is the nucleic acid of interest that may be present in the sample. In some embodiments, the target nucleic acid is a gene or a gene fragment. In other embodiments, the target nucleic acid contains a genetic variant, e.g., a polymorphism, including a single nucleotide polymorphism or variant (SNP of SNV), or a genetic rearrangement resulting e.g., in a gene fusion. In some embodiments, the target nucleic acid comprises a biomarker. In other embodiments, the target nucleic acid is characteristic of a particular organism, e.g., aids in identification of the pathogenic organism or a characteristic of the pathogenic organism, e.g., drug sensitivity or drug resistance. In yet other embodiments, the target nucleic acid is characteristic of a human subject, e.g., the HLA or KIR sequence defining the subject's unique HLA or KIR genotype. In yet other embodiments, all the sequences in the sample are target nucleic acids e.g., in shotgun genomic sequencing.

In an embodiment of the invention, a double-stranded target nucleic acid is converted into the template configuration of the invention. In some embodiments, the target nucleic acid occurs in nature in a single-stranded form (e.g., RNA, including mRNA, microRNA, viral RNA; or single-stranded viral DNA). The single-stranded target nucleic acid is converted into double-stranded form to enable the further steps of the claimed method.

Longer target nucleic acids may be fragmented although in some applications longer target nucleic acids may be desired to achieve a longer read. The present invention is especially advantageous for longer nucleic acid targets.

In some embodiments, the invention comprises a target enrichment step. The enrichment may be by capturing the target sequences via one or more targets-specific probes. The nucleic acids in the sample may be denatured and contacted with single-stranded target-specific probes. The probes may comprise a ligand for an affinity capture moiety so that after hybridization complexes are formed, they are captured by providing the affinity capture moiety. In some embodiments, the affinity capture moiety is avidin or streptavidin and the ligand is biotin. In some embodiments, the moiety is bound to solid support. As described in further detail below, the solid support may comprise superparamagnetic spherical polymer particles such as DYNABEADS™ magnetic beads or magnetic glass particles.

In some embodiments of the present invention, adaptor molecules are ligated to the target nucleic acid. The ligation can be a blunt-end ligation or a more efficient cohesive-end ligation. The target nucleic acid may be rendered blunt-ended by "end repair" comprising strand-filling, i.e., extending a 3'-terminus by a DNA polymerase to eliminate a 5'-overhang. In some embodiments, the blunt-ended nucleic acids may be rendered cohesive by addition of a single nucleotide to the 3'-end of the adaptor and a single complementary nucleotide to the 3'-ends of the target nucleic acid, e.g., by a DNA polymerase or a terminal transferase. In yet other embodiments, the adaptors and the target nucleic acid may acquire cohesive ends (overhangs) by digestion with restriction endonucleases. The restriction enzyme recognition site may be inherent or engineered into the sequences. In some embodiments, other enzymatic steps may be required to accomplish the ligation. In some embodiments, a polynucleotide kinase may be used to add 5'-phosphates to the target nucleic acid molecules and adaptor molecules.

In some embodiments, the adaptor is shown in FIG. 1 is used. The adaptor has a single-stranded and a double-stranded region wherein the single-stranded region comprises a primer binding site (e.g., a sequencing primer binding site). To enable ligation of the adaptor to the double-stranded target nucleic acid, the 5'-end of the adaptor may be phosphorylated. To prevent degradation of the shorter strand of the adaptor by the polymerase extending the sequencing primer bound to the sequencing primer binding site, the 3'-end of the shorter strand of the adaptor may contain modified nucleotides at or near the 3'-end of the shorter strand. In some embodiments, the modified nucleotide is a phosphorothioate nucleotide.

In some embodiments, the double stranded region of the adaptor comprises modified nucleotides that modify (e.g., increase) the melting temperature ($T_m$) of the adaptor molecule. In some embodiments, the modified nucleotide is modified pyrimidine such as methyl-dC or propynyl-dU. In some embodiments, the modified nucleotide is a modified purine, e.g., G-clamp.

In some embodiments, the primer binding site in the single-stranded region of the adaptor comprises modified nucleotides that modify (e.g., increase) the melting temperature ($T_m$) of the primer bound to the primer binding site. In some embodiments, the modified nucleotide is modified pyrimidine such as methyl-dC or propynyl-dU. In some embodiments, the modified nucleotide is a modified purine, e.g., G-clamp.

FIG. 1 illustrates an example of the sequence and structure of the linear adaptor. The adaptor includes a short double stranded portion with a 5'-phosphate and a single 3'-T overhang to facilitate ligation to the target insert. The adaptor includes a long arm with phosphorothioate modifications (asterisk) to avoid digestion by the 5'-3' exonuclease activity of the DNA polymerase. The long arm further contains a binding site for a sequencing primer to enable polymerase binding and sequencing of the target insert.

FIG. 2 illustrates sequencing a single long target sequence with the adaptor shown in FIG. 1. Linear adaptors are ligated at both ends of the template with the arrow showing the direction of sequencing into the template. Consensus will be achieved using reads from multiple pores (intermolecular consensus).

Figure 3:
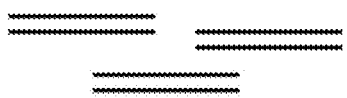
FIG. 3 illustrates a concatenation strategy for short target sequences using adaptors shown in FIG. 1 or FIG. 4.
Figure 3:

FIG. 3 illustrates a concatenation strategy for short target sequences. Adaptors with unique molecular IDs (UIDs) are ligated to each target sequence prior to concatenation. Consensus can be achieved using reads from multiple pores and within each read, using UIDs.

Figure 4:
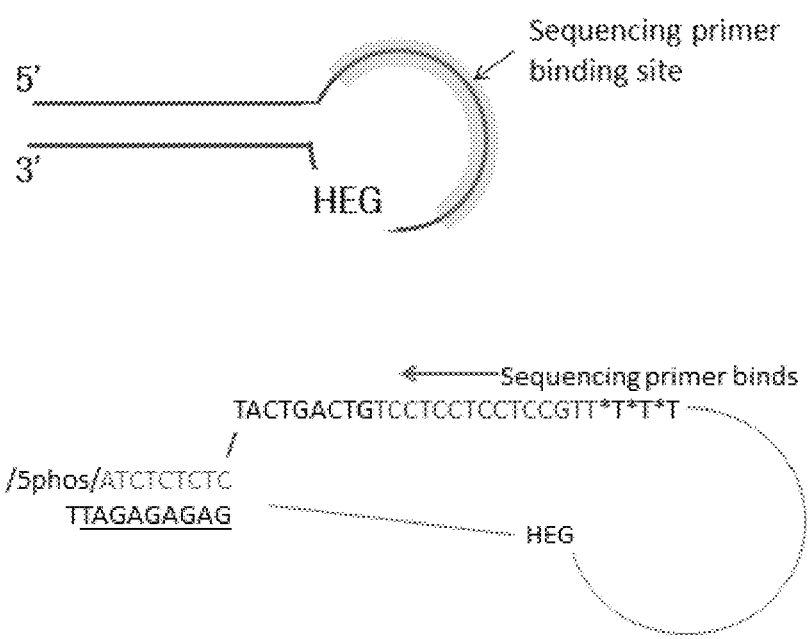
FIG. 4 illustrates the novel adaptor of FIG. 1 with a non-nucleotide linker.

FIG. 4 illustrates the sequence and structure of an adaptor having an 18-carbon non-nucleotide linker (HEG).

In some embodiments, the adaptor molecules are in vitro synthesized artificial sequences. In other embodiments, the adaptor molecules are in vitro synthesized naturally-occurring sequences. In yet other embodiments, the adaptor molecules are isolated naturally occurring molecules.

In some embodiments, the method comprises a step of amplifying the target nucleic acid prior to adaptor ligation. The amplification may be by exponential polymerase chain reaction (PCR), linear amplification of only one strand or any other method that utilizes oligonucleotide primers. Various PCR conditions are described in *PCR Strategics* (M. A. Innis, D. H. Gelfand, and J. J. Sninsky eds., 1995, Academic Press, San Diego, CA) at Chapter 14; *PCR Protocols: A Guide to Methods and Applications* (M. A. Innis, D. H. Gelfand, J. J. Sninsky, and T. J. White eds., Academic Press, NY, 1990).

In some embodiments, amplification utilizes a universal primer binding site introduced into the target sequence. In other embodiments, a gene-specific (target-specific) primer or primer pair is used. Amplified target nucleic acids are ligated to the adaptors as described herein.

In some embodiments, the target nucleic acids are concatenated into longer nucleic acids. For example, shorter nucleic acids, shorter than 1 kilobase-long (e.g., 100, 200, 300, etc. bases long) can be concatenated into a fragment that is several kilobases long. Prior to concatenation, the ends of the target nucleic acids are ligated to a double stranded adaptor containing a barcode. The resulting concatenate is a molecule comprising two or more target nucleic acid sequences punctuated by adaptor sequences. If copies of the same target nucleic acid are concatenated, a consensus sequence can be built out of a single read of such concatenate.

In some embodiments, concatenation is accomplished by digestion of the adaptor ends with a Type II restriction enzyme at the specific restriction enzyme recognition sites. The enzyme generates cohesive ends allowing for multiple adapted target nucleic acids to be ligated with a DNA ligase. In other embodiments, concatenation is accomplished independent of the nucleic acid sequence by the Gibson assembly method (Gibson et al., (2009), *Enzymatic assembly of DNA molecules up to several hundred kilobases, Nature Methods*, 6(5): 343-348 and U.S. Pat. No. 8,968,999.

In some embodiments, the invention comprises introduction of barcodes into the target nucleic acids. Sequencing individual molecules typically requires molecular barcodes such as described e.g., in U.S. Pat. Nos. 7,393,665, 8,168,335, 8,481,292, 8,685,678, and 8,722,368. A unique molecular barcode is a short artificial sequence added to each molecule in a sample such as a patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy. See U.S. patent application Ser. Nos. 14/209,807 and 14/774,518. Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample. See Id.

In some embodiments, adaptors comprise one or more barcodes. In other embodiments, amplification primers (e.g., those used in amplification prior to adaptor ligation) comprise barcodes in the 5'-portion of the primer. A barcode can be a multiplex sample ID (MID) used to identify the source of the sample where samples are mixed (multiplexed). The barcode may also serve as a unique molecular ID (UID) used to identify each original molecule and its progeny. The barcode may also be a combination of a UID and an MID. In some embodiments, a single barcode is used as both UID and MID.

In some embodiments, each barcode comprises a predefined sequence. In other embodiments, the barcode comprises a random sequence. Barcodes can be 1-20 nucleotides long.

In some embodiments, the invention is a method of making a library of sequencing-ready adapted double-stranded target nucleic acids as described herein and the library produced by the method. Specifically, the library comprises a collection of adapted double-stranded molecules derived from nucleic acids present in a sample. The molecules of the library comprise target sequences joined with adaptor sequences.

In some embodiments, the present invention comprises detecting target nucleic acids in a sample by nucleic acid sequencing. Multiple nucleic acids, including all the nucleic acids in a sample may be converted into the template configuration of the invention and sequenced. In some embodiments, the library of single stranded circular molecules can be subjected to nucleic acid sequencing.

In some embodiments, the method further comprises a step of eliminating damaged or degraded targets in order to improve the quality and length of sequencing reads. The step may comprise contacting the reaction mixture with uracil DNA N-glycosylase (UNG or UDG) or AP nuclease in order to degrade such damaged target nucleic acids. In some embodiments, the method further comprises a step of eliminating damaged or degraded targets from the library in order to improve the quality and length of sequencing reads. The step may comprise contacting the library with one or more of uracil DNA N-glycosylase (UNG or UDG), AP nuclease and Fpg (formamidopyrimidine [fapy]-DNA glycosylase), also known as 8-oxoguanine DNA glycosylase in order to degrade such damaged target nucleic acids.

As described above, the adaptor or the target-specific primer may comprise a sequencing primer binding site which can initiate a sequencing read of each strand.

Sequencing can be performed by any method known in the art. Especially advantageous is the high-throughput single molecule sequencing capable of reading circular target nucleic acids. Examples of such technologies include the Pacific BioSciences platform utilizing the SMRT (Pacific Biosciences, Menlo Park, Cal.) or a platform utilizing nanopore technology such as those manufactured by Oxford Nanopore Technologies (Oxford, UK) or Roche Sequencing Solutions (Genia) (Santa Clara, Cal.) and any other presently existing or future DNA sequencing technology that does or does not involve sequencing by synthesis. The sequencing step may utilize platform-specific sequencing primers. Binding sites for these primers may be introduced in the method of the invention as described herein, i.e., by being a part of second adaptors or amplification primers.

Analysis and Error Correction

In some embodiments, the sequencing step involves sequence analysis including a step of sequence aligning. In some embodiments, aligning is used to determine a consensus sequence from a plurality of sequences, e.g., a plurality having the same barcodes (UID). In some embodiments barcodes (UIDs) are used to determine a consensus from a plurality of sequences all having an identical barcode (UID).

In other embodiments, barcodes (UIDs) are used to eliminate artifacts, i.e., variations existing in some but not all sequences having an identical barcode (UID). Such artifacts resulting from PCR errors or sequencing errors can be eliminated.

In some embodiments, the number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

In some embodiments, the invention comprises a step of building a consensus sequence based on multiple reads of a target nucleic acid. In some embodiments, each copy of the target nucleic acid is ligated to adaptors and sequenced once. The consensus sequence is assembled intermolecularly by comparing reads of several copies of a target nucleic acid each of which has been read once. For example, nucleic acids that are about 1 kb long or longer are sequenced in this way. In some embodiments, several copies of the target nucleic acid are ligated together (concatenated). The concatenate is then ligated to adaptors and sequenced once. The consensus sequence is assembled intramolecularly by comparing reads from the several copies of the target nucleic acid within the concatenate. For example, nucleic acids that are less than 1 kb long are sequenced in this way.

EXAMPLES

Example 1. Template Preparation

The sequencing template was linearized pUC19 plasmid DNA (2.7 kb) or a 500 bp and a 1.15 kb HIV amplicon. The input DNA was quantified using Qubit fluorometric analysis (ThermoFisher Scientific). Bioanalyzer with a DNA 12000 kit (Agilent Technologies, Santa Clara, Cal.) was used to assess DNA size, quality and quantity. A clean-up was performed using KAPA PureBeads (KAPA Biosystems, Inc., Wilmington, Mass.) purification according to the manufacturer's instructions.

Example 2. Library Preparation and Sequencing on Pacific Biosciences RSII Platform Template DNA (1 ug plasmid or amplicon) was prepared for adaptor ligation using KAPA HyperPrep kit Library Preparation. Briefly, the purified linearized plasmid DNA was end-repaired and A-tailed according to the manufacturer's instructions. This step was followed immediately by adaptor ligation using linear adaptors or the HEG adaptors (FIG. 1 or FIG. 4). In the same tube, ligation mastermix and adaptors were added and the reaction mixture was incubated at 20° C. for 30 minutes. Ligase enzyme was inactivated by a further incubation at 65° C. for 10 min. All adaptors were present at a template:adaptor ligation ratio of 1:200. Ligation was followed by a final 0.8×KAPA Purebeads bead clean-up step. The library yields were quantified using Qubit fluorometric analysis (Life Technologies) and checked for size using the Bioanalyzer HS kit (Agilent Technologies, Santa Clara, CA). Purified adapted templates were sequenced on the Pacific Biosciences RSII platform according to the manufacturers' instructions and on Roche nanopore Platform. RSII Results are shown in Table 1 with different sized amplicons and Table 2 shows results on the Roche Nanopore platform.

TABLE 1

RSII Results

| Template | Polymerase Read Length (bases) | Reads of Interest Length (bases) | # High Quality Reads |
| --- | --- | --- | --- |
| 500 bp amplicon with Linear adaptor - Replicate 1 | 574 | 574 | 8440 |
| 500 bp amplicon with Linear adaptor - Replicate 2 | 615 | 615 | 8821 |
| 1.15 kb amplicon with Linear adaptor - Replicate 1 | 1268 | 1268 | 31800 |
| 1.15 kb amplicon with Linear adaptor - Replicate 2 | 1292 | 1293 | 33858 |
| 2.7 kb amplicon with Linear adaptor - Replicate 1 | 2339 | 2336 | 12244 |
| 2.7 kb amplicon with Linear adaptor - Replicate 2 | 2409 | 2406 | 11927 |

TABLE 2

Nanopore results

| Template (# of Sequencing Runs) | % Aligned reads from the High Quality Regions of SINGLE PORES | Median Procession Length (bp) |
| --- | --- | --- |
| Control (n = 4) | 44.88 ± 0.43 | 1664 ± 78 |
| Control (n = 3) | 29.39 ± 1.26 | 1769 ± 40 |
| Control (n = 3) | 45.24 ± 2.96 | 1525 ± 79 |
| Control (n = 4) | 23.63 ± 3.66 | 1765 ± 129 |
| Linear adaptor (n = 2) | 33.15 ± 0.33 | 2423 ± 13 |
| Linear adaptor (n = 4) | 34.46 ± 2.03 | 2043 ± 67 |
| Linear adaptor (n = 8) | 30.53 ± 2.18 | 2162 ± 147 |
| Linear adaptor (n = 6) | 30.66 ± 1.77 | 1856 ± 178 |
| Linear adaptor (n = 5) | 31.71 ± 0.32 | 2352 ± 86 |

Example 3. Sequencing Concatenated Linear Templates Using Novel Adaptors

In this example, the starting target sequence was a 187 bp long NRAS exon 3 amplicon and this amplicon was concatenated, ligated to novel adaptors (FIG. 1) and sequenced. The control for this experiment was a pUC2.7 kb plasmid and ligated with SMRTBell™ adaptors to generate a circular library. To further test robustness of concatenation, we concatenated different sized oncology amplicons. Eleven additional oncology amplicons (of different sizes) were concatenated, ligated to novel adapters and sequenced on the nanopore platform. The 11 amplicons were NRAS exon3, NRAS exon4.1, NRAS exon4.2, KRAS exon2, KRAS exon3, KRAS exon4, BRAF exon11, PIK3CA exon9, EGFR exon18, EGFR exon20, EGFR exon21. The templates were sequenced on RSII and the Roche Nanopore platform. Results from the RSII instrument are shown in Table 3 and results from the Roche Nanopore platform are shown in Table 4.

Sequencing Concatenated Templates

TABLE 3

RSII Results

| Template | Polymerase Read Length (bases) | Reads of Interest Length (bases) | # High Quality Reads |
|---|---|---|---|
| One amplicon Concatemer (NRAS; 180 bp)- Linear adaptor | 2047 | 2048 | 49780 |
| One amplicon Concatemer (NRAS; 180 bp)- Linear adaptor | 2013 | 2013 | 47670 |
| 11 amplicon Concatemer - SMRTBell adaptor (control) - Replicate 1 | 18015 | 993 | 98261 |
| 11 amplicon Concatemer - SMRTBell adaptor (control) - Replicate 2 | 17397 | 1029 | 92616 |
| 11 amplicon Concatemer -Linear adaptor - Replicate 1 | 1431 | 1432 | 36201 |
| 11 amplicon Concatemer - Linear adaptor - Replicate 2 | 1109 | 1109 | 23293 |

TABLE 4

Nanopore Results

| Template (# of Sequencing Runs) | Single Pores that formed | All single pores with library(DNA) | # High quality single reads |
|---|---|---|---|
| Control {Plasmid pUC2.7 kb DNA with a SMRTBell ™ adapter i.e. circular library (n = 4)} | 6233 | 1726 | 1152 |
| Control {Plasmid pUC2.7 kb DNA with a SMRTBell ™ adapter i.e. circular library (n = 3)} | 7979 | 2447 | 1582 |
| One amplicon Concatemer - Linear adaptor (run#1) | 5886 | 1175 | 816 |
| One amplicon Concatemer - Linear adaptor (run#2) | 7500 | 1606 | 909 |
| One amplicon Concatemer - Linear adaptor (run#3) | 6207 | 1927 | 1215 |
| 11 amplicon Concatemer - Linear adaptor (run#1) | 6369 | 1476 | 1045 |
| 11 amplicon Concatemer - Linear adaptor (run#2) | 7086 | 1108 | 754 |
| 11 amplicon Concatemer Linear adaptor (run#3) | 4777 | 1835 | 1378 |

Example 4. Constructing and Sequencing HEG Adaptor Library

In this example, linearized plasmid pUC19 (2.7 kb) was used. Novel dumbbell shaped adaptors that used a hexaethylene glycol (HEG) 18-carbon linker (FIG. 4) were used to make libraries. SMRTBell adaptors were used as a control. 50 uM of linear or HEG adaptors were used during library preparation. The HEG/linear adapter ligated library was incubated with a biotinylated Sequencing Primer to anneal at 45° C. for 30 seconds and was cooled to 20° C. with ramp rate at 0.1° C./s. This was followed by (Polymerase-and-Pore) complex binding. Enrichment was achieved by using Streptavidin-coupled beads to bind to the biotinylated primer-complex and enrich the sequencing-ready complex. Sequencing was performed on the Roche nanopore platform. Results are shown in Table 5.

TABLE 5

Sequencing HEG adaptor library on the nanopore system

| Template (# of Sequencing Runs) | % Aligned reads from the High Quality Regions of SINGLE PORES | Median Procession Length (bp) |
|---|---|---|
| HEG Adaptor Library #1 | 42.04% | 2555 |
| HEG Adaptor Library #2 | 33.61% | 2264 |
| HEG Adaptor Library #3 | 42.34% | 2476 |
| HEG Adaptor Library #4 | 40.78% | 2478 |
| HEG Adaptor Library #5 | 43.07% | 2413 |
| HEG Adaptor Library #6 | 41.66% | 2367 |
| Average - HEG Adaptor (n = 6) | 40.58% | 2425.5 |
| Dumbbell Adaptor Library #1 | 27.28% | 2219 |
| Dumbbell Adaptor Library #2 | 21.77% | 2508 |
| Dumbbell Adaptor Library #3 | 16.65% | 2167 |
| Dumbbell Adaptor Library #4 | 29.07% | 2494 |
| Dumbbell Adaptor Library #5 | 27.35% | 2569 |
| Average - Dumbbell Adaptor (n = 5) | 24.43% | 2391.40 |

The invention claimed is:

1. A method of separately sequencing each strand of a double-stranded target nucleic acid comprising the steps of:
   (a) in a reaction mixture, joining a double-stranded target nucleic acid to adaptors to form an adapted double-stranded target nucleic acid wherein the adaptor has a 5'-end and a 3'-end, and comprises a double-stranded region, a non-nucleotide linker and a single-stranded region, wherein the single-stranded region comprises a sequencing primer-binding site;
   (b) annealing a sequencing primer to the sequencing primer-binding site in the adaptor; and
   (c) extending the sequencing primer, thereby sequencing each strand of the adapted double-stranded target nucleic acid.

2. The method of claim 1, wherein the non-nucleotide linker is a polyethylene glycol.

3. The method of claim 2, wherein the polyethylene glycol is hexaethylene glycol (HEG).

4. The method of claim 1, wherein the 3'-end of the adaptor comprises a modification inhibiting enzymatic degradation.

5. The method of claim 4, wherein the modification comprises at least one phosphorothioate group.

6. The method of claim 1, wherein the double-stranded region or the single-stranded region of the adaptor comprises one or more modified nucleotides that increase the melting temperature ($T_m$) of the adaptor.

7. The method of claim 6, wherein the modified nucleotide is selected from methyl-dC, propynyl-dU, and G-clamp.

8. The method of claim 1, further comprising a target enrichment step.

9. The method of claim 8, wherein the enrichment is by capture via target-specific probes bound to a solid support.

10. The method of claim 1, further comprising prior to step (b), contacting the reaction mixture with a DNA damage-specific cleavage agent selected from glycosylase and endonuclease, thereby cleaving damaged DNA.

11. The method of claim 1, wherein the adaptor comprises one or more barcodes selected from unique ID (UID) and sample multiplexing ID (MID).

12. The method of claim 1, wherein the target nucleic acid comprises a concatenate of two or more copies of the target sequence.

13. The method of claim 12, further comprising a step of building a consensus sequence of the target nucleic acid from the sequence of the concatenate.

* * * * *